United States Patent
Koo

(10) Patent No.: US 10,150,978 B2
(45) Date of Patent: Dec. 11, 2018

(54) METHOD OF MANUFACTURING CELLULOSIC SUGAR FROM BIOMASS THROUGH EFFECTIVE SEPARATION OF IMPURITIES AND SUGAR

(71) Applicant: SK Innovation Co., Ltd., Seoul (KR)

(72) Inventor: Min Su Koo, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 15/342,356

(22) Filed: Nov. 3, 2016

(65) Prior Publication Data

US 2017/0121745 A1   May 4, 2017

(30) Foreign Application Priority Data

Nov. 4, 2015  (KR) .................... 10-2015-0154695

(51) Int. Cl.
*C12P 19/02* (2006.01)
*C12P 19/14* (2006.01)

(52) U.S. Cl.
CPC ............. *C12P 19/02* (2013.01); *C12P 19/14* (2013.01); *C12P 2201/00* (2013.01)

(58) Field of Classification Search
None
See application file for complete search history.

(56) References Cited

U.S. PATENT DOCUMENTS

| 2,944,923 A | * | 7/1960 | Riehm | ............... B01D 1/00 |
| | | | | 127/37 |
| 2009/0098616 A1 | | 4/2009 | Burke et al. | |
| 2010/0069626 A1 | | 3/2010 | Kilambi | |

FOREIGN PATENT DOCUMENTS

| KR | 101273218 B1 | 6/2013 |
| KR | 10139412 B1 | 5/2014 |
| KR | 101392736 B1 | 5/2014 |

OTHER PUBLICATIONS

Qing et al. Biotechnology for biofuels (2011), 4: p. 18.*
Agbogbo et al. 2006, Process Biochemistry, 41: 2333-2336.*
Senac et al. Appl and Environ Microbiol (1990), 56(1): 120-126.*
Lee et al. Biomass and Bioenergy (2011), 35, :626-636.*
Choi et al. Bioresource Technology (1996), 58: 101-106.*

* cited by examiner

*Primary Examiner* — Iqbal H Chowdhury
(74) *Attorney, Agent, or Firm* — The Webb Law Firm

(57) ABSTRACT

The present invention relates to a method of producing cellulosic sugar from biomass by effective impurity removal and sugar separation, and more particularly to a method for producing cellulosic sugar from biomass. The method includes pretreating the biomass so as to be separated into a solid and a liquid; subjecting the separated liquid to monomerization, concentration and adsorption processes, thereby obtaining xylose; and subjecting the separated solid to second pretreatment, saccharification and lignin separation processes, thereby obtaining glucose. The method allows fermentation inhibitory substances to be removed from pretreated biomass in a cost- and energy-effective process, and is useful for effective production of cellulosic sugar.

6 Claims, 1 Drawing Sheet

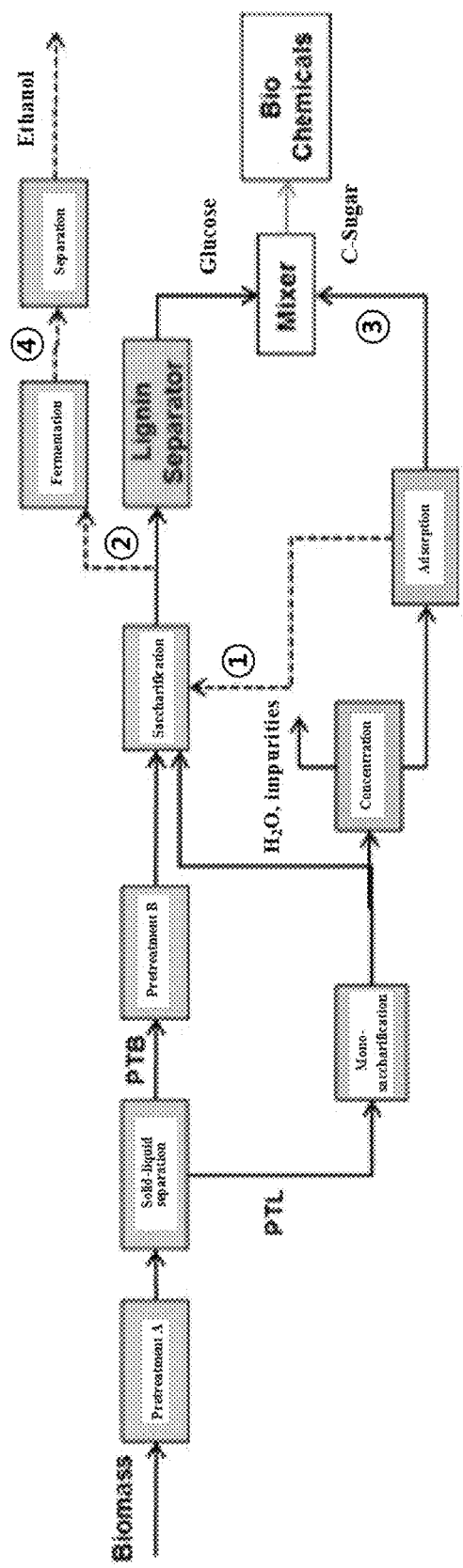

METHOD OF MANUFACTURING CELLULOSIC SUGAR FROM BIOMASS THROUGH EFFECTIVE SEPARATION OF IMPURITIES AND SUGAR

CROSS-REFERENCE TO RELATED APPLICATION

This application claims priority to Korean Patent Application No. 10-2015-0154695 filed Nov. 4, 2015, the disclosure of which is hereby incorporated in its entirety by reference.

TECHNICAL FIELD

The present invention relates to a method of producing cellulosic sugar (hereinafter referred to as "C-sugar") from biomass by effective impurity removal and sugar separation, and more particularly to a method for producing C-sugar from biomass, comprising: pretreating the biomass so as to be separated into a solid and a liquid; subjecting the separated liquid to monomerization, concentration and adsorption processes, thereby obtaining xylose; and subjecting the separated solid to second pretreatment, saccharification and lignin separation processes, thereby obtaining glucose.

BACKGROUND ART

Cellulosic biomass has advantages in that it is abundant, renewable and inexpensive, and due to such advantages, the possibility of using the cellulosic biomass as a raw material for fuel alcohol such as ethanol or butanol is increasing. Cellulosic biomass comprises cellulose, hemicellulose and lignin as main components, which are strongly bonded to one another. Thus, in order to produce C-Sugar from the biomass in high yield, these three components need to be separated from one another by pretreatment.

Among the three components, cellulose has the properties of being thermally stable and being soluble in acid, and hemicellulose has the properties of being thermally unstable and being soluble in acid. On the other hand, lignin has the properties of being thermally stable and being soluble in alkali.

In order to efficiently separate these components from one another, which have different properties as described above, various pretreatment processes have been developed. Generally, a general pretreatment method is to selectively remove the hemicellulose and lignin components without loss of the cellulose component to thereby convert the cellulosic raw material into a form easy to enzymatically saccharify.

Major pretreatment methods include mechanical crushing, alkali swelling, dilute acid hydrolysis, hydrothermal pretreatment and steam explosion pretreatment methods, and combinations of such methods may also be used.

Among these methods, the hydrothermal pretreatment method can separate hemicellulose as a liquid by water under mild operating conditions while allowing cellulose and lignin to remain as a solid. It is a method that increases the recovery of hemicellulose having low thermal stability by the use of mild operating conditions.

Furthermore, in the steam explosion pretreatment method, a raw material is charged into a pressurized reactor and saturated stream is blown into the reactor to cause a pressurized reaction, and then pressure is suddenly discharged from the reactor, whereby an exploded raw material can be obtained. In this procedure, saccharification of hemicellulose may occur, or the structure of lignin may also be broken. This method has high energy efficiency, because the raw material does not need to be finely crushed.

Once the cellulose, hemicellulose and lignin components are separated from one another by the above-described pretreatment method, the cellulose component is subjected to an enzymatic saccharification step.

The enzyme that is involved in the saccharification is a catalyst having very high substrate selectivity, and the enzymatic reaction conditions are very mild so that the load in reactor design and operations is reduced. Cellulose saccharification is based on three actions. Endo-β-1,4-glucanase, exo-β-1,4-glucanase and β-glucosidase randomly attack cellulose to separate cellobiose from cellulose chain ends. When the antagonism between endo-β-1,4-glucanase and exo-β-1,4-glucanase is continued, the concentration of the cellobiose increases, and the activity of exo-β-1,4-glucanase is severely inhibited by accumulation of the cellobiose. The produced cellobiose is then cleaved to glucose by β-glucosidase. This cleavage procedure proceeds in a liquid phase. In addition, while the glucose is accumulated, β-glucosidase is also inhibited. Saccharification of the cellulose is influenced by all the three enzymes as described above.

However, it is well known that when fermentable sugar is produced from cellulosic biomass by pretreatment and saccharification processes, substances (acetic acid, HMF, furfural, etc.) capable of inhibiting fermentation are produced in the pretreatment process (degeneration occurs mainly in a high-temperature and high-pressure reaction), and particularly, when hydrothermal treatment is carried out, a large amount of a xylo-oligomer occurs after pretreatment to thereby inhibit enzymatic saccharification.

Korean Patent No. 1393412 discloses a method of producing a hydrolysate from cellulosic biomass by alkali soaking-steam pretreatment, which can recover useful substances. In the above patent document, alkali-based pretreatment rather than hydrothermal pretreatment is performed to thereby minimize the production of fermentation inhibitory substances by hydrothermal pretreatment, but there are disadvantages in that the separation process is complicated due to the use of the alkaline substance and in that the efficiency of saccharification and fermentation can be reduced if the alkaline substance is not removed to a suitable concentration or lower.

Korean Patent No. 1392736 discloses an integrated process for production of bioethanol, which includes lignocellulosic biomass pretreatment using nitric acid prepared from nitric oxide. In this patent document, biomass is pretreated with nitric acid so that the production of fermentation inhibitory substances by hydrothermal pretreatment is minimized. However, there are also disadvantages in that the process is complicated due to separation of the acidic substance and in that the efficiency of saccharification can be reduced if the acidic substance is not removed to a certain concentration or lower.

Korean Patent No. 10-1273218 discloses a steam-explosion pretreatment method. In the method disclosed in this patent document, steam is blown into a reactor to pressurize the reactor, and then pressurize is suddenly discharged from the reactor to cause explosion to thereby break the structure of a raw material after pretreatment. Thus, a chip-type raw material having a size of about 2 cm×2 cm×1 cm can be used without pulverization, and energy required for pulverization can be saved, unlike the case of other pretreatments, and a strong biomass structure can be broken to facilitate its contact with an enzyme, thus increasing the efficiency of saccharification. However, there are disadvantages in that, because a pressurization process should be used in the explosion step, the overall process is complicated and a large amount of energy is consumed.

Accordingly, the present inventors have made extensive efforts to solve the above-described problems, and as a result, have found that, when biomass is pretreated so as to be separated into a solid and a liquid and the separated solid and liquid are subjected to a saccharification process and a monomerization process, respectively, to produce glucose and xylose, fermentation inhibitory substances can be removed in a cost- and energy-effective process, thereby completing the present invention.

DISCLOSURE OF INVENTION

Technical Problem

It is an object of the present invention to provide a method of producing C-Sugar from biomass by effective impurity removal and sugar separation.

Technical Solution

To achieve the above object, the present invention provides a method for producing cellulosic sugar from biomass by impurity removal and sugar separation, the method comprising the steps of: (a) pretreating the biomass, and then separating pretreated liquid (PTL) containing a xylo-oligomer (enzymatic saccharification inhibitor) as a main component and into a pretreated biomass (PTB) containing cellulose and lignin as main components; (b) monosacchrifying the PTL, concentrating the monomerized PTL to remove first impurities, and then removing second impurities from the PTL by adsorption, thereby obtaining xylose; and (c) secondly pretreating the PTB, saccharifying the pretreated PTB by an enzyme, and then separating lignin from a hydrolysate, thereby obtaining glucose.

Advantageous Effects

The method of producing cellulosic sugar from biomass by effective impurity removal and sugar separation according to the present invention allows fermentation inhibitory substances to be removed from pretreated biomass in a cost- and energy-effective process, and thus is useful for effective production of cellulosic sugar.

BRIEF DESCRIPTION OF THE DRAWINGS

FIG. 1 is a schematic diagram showing a production process according to the present invention.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, biomass was pretreated so as to be separated into a solid and a liquid, and the separated solid and liquid were subjected to an enzymatic saccharification process and a monomerization process, respectively, to produce glucose and xylose. As a result, it has been found that fermentation inhibitory substances can be removed in a cost- and energy-effective process, and thus a high concentration of C-Sugar can be produced.

Therefore, in one aspect, the present invention is directed to a method for producing cellulosic sugar from biomass by impurity removal and sugar separation, the method comprising the steps of: (a) pretreating the biomass, and then separating pretreated liquid (PTL) containing a xylo-oligomer (enzymatic saccharification inhibitor) as a main component and into a pretreated biomass (PTB) containing cellulose and lignin as main components; (b) monosacchrifying the PTL, concentrating the monomerized PTL to remove first impurities, and then removing second impurities from the PTL by adsorption, thereby obtaining xylose; and (c) secondly pretreating the PTB, saccharifying the pretreated PTB by an enzyme, and then separating lignin from a hydrolysate, thereby obtaining glucose.

Sugar produced by biomass pretreatment is separated by a solid-liquid separator into a liquid (PTL) containing a xylo-oligomer as a main component and into a solid containing cellulose and lignin as main components. Because the PTL contains a significant amount of the xylo-oligomer (enzymatic saccharification inhibitor), it is monomerized in a monomerization reactor to produce xylose. Herein, the PTL that passed through the monomerization reactor has high water content, and thus has the effect of diluting the concentration of sugar when being introduced directly into a subsequent process, and for this reason, it needs to be concentrated. In addition, the PTL contains a large amount of fermentation inhibitory substances, and thus has the possibility of inhibiting fermentation when being introduced directly into a biochemical fermentation process, and for this reason, the concentration of the fermentation inhibitory substances needs to be reduced depending on the user.

The method of the present invention may further comprise a step of introducing a non-saccharified substance resulting from the adsorption of step (b) into the saccharification process of step (c) (path ① in FIG. 1). If the temperature of the reaction for converting the xylo-oligomer to xylose in the monomerization process of step (b) is increased, the convention rate can be increased but the xylose selectivity can be reduced. Thus, if the reaction is carried out at low temperature in order to increase the xylose selectivity, the reaction product may contain an unreacted non-saccharified substance (xylo-oligomer). Thus, this component may be introduced into the enzymatic saccharification process of step (c) so that the non-saccharified xylo-oligomer can be saccharified, thereby increasing the xylose saccharification yield.

In addition, the method of the present invention may further comprise, after the monomerization process of step (b), a step of introducing a portion of the monomerized PTL into the saccharification process of step (c). In order to increase the concentrations of xylose and glucose produced, the PTL, subjected to the monomerization, concentration and adsorption processes, may be supplied instead of using pure water to adjust the water content of the PTB before saccharification. If the sugar concentration of the saccharification solution is increased, C-Sugar may be supplied to the user without additional concentration. If path ② in FIG. 1 is applied, the concentration of bioethanol that is produced by fermentation can be increased, and thus energy required for a bioethanol separation process can be reduced.

In the present invention, the concentration of step (b) may be a vacuum concentration process, and the first impurities may be one or more selected from among acetic acid, hydroxymethyl furfural (HMF), and furfural. Herein, the HMF is generally produced by dehydration of hexose, and furfural is produced by dehydration of pentose.

In addition, the PTL after the monomerization reaction (about 90 to 140° C.) needs to be cooled before introduction into an additional subsequent process. However, when the PTL is supplied to a concentration process without cooling so as to replace a portion of heat to be supplied to a concentration column, energy required for the concentration can be reduced. In addition, when concentration column is operated under a vacuum, water and fermentation inhibitory substances can be easily removed by evaporation, and the decomposition loss of xylose by heat can be prevented. Simulation process results indicated that when the concentration is performed under a vacuum of 10-300 torr, energy can be reduced by 25-30% compared to when the concentration is performed at atmospheric pressure.

Herein, the concentration process may be performed until any concentration satisfying the fermentation inhibitory substance limit required by the user is reached.

In the present invention, the vacuum concentration may be performed at 10-300 torr. If the vacuum concentration is performed at lower pressure, the amount of energy to be supplied can be reduced, and higher concentration can be achieved, but the consumption of energy for maintaining the vacuum increases as the pressure decreases. For this reason, the concentration process is preferably performed in a suitable degree of a vacuum. Herein, if the vacuum level is lower than 10 torr, the amount of energy required to maintain the vacuum level or to reduce pressure to the vacuum level will increase rapidly, and a vacuum level higher than 300 torr is used, it can reduce the effect of vacuum concentration and result in the loss of xylose.

In the present invention, the adsorption of step (b) may be performed using activated carbon as an adsorbent, and the second impurities may be one or more selected from among acetic acid and hydroxymethyl furfural (HMF). Fermentation inhibitory substances such as furfural can be completely removed by concentration. However, in the case of some fermentation inhibitory substances such as acetic acid and HMF, the absolute amount thereof can be reduced by concentration, but the amount thereof relative to the sugar concentration and the water content increases rather than decreases. For this reason, the remaining fermentation inhibitory substances are removed by an adsorption process, so that a final product containing the fermentation inhibitory substances at desired concentrations or lower can be supplied. For example, if fermentation inhibitory substances that inhibits the performance of a fermentation strain are included in a fermentation process (for example, in the case of yeast, acetic acid: 5 g/L or more, and the total amount of furfural and HMF: 1 g/L or more), no fermentation will occur. For this reason, if the fermentation inhibitory substances are removed by this adsorption process, fermentation will be stably performed so that the fermentation rate will significantly increase (2-5%), and the initial fermentation time can be reduced to increase productivity.

In the present invention, the concentration of xylose in step (b) may be 5-50 wt %, and the concentration of glucose in step (c) may be 5-12 wt %.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Production of Hydrolysate by Sugar Separation and Fermentation Inhibitor Removal As shown in FIG. 1, biomass was crushed and pretreated to produce C-Sugar which was then separated into a liquid (PTL) containing a xylo-oligomer (enzymatic saccharification inhibitor) as a main component and into a solid (PTB) containing cellulose and lignin as main components. Next, the PTB was further pretreated, and then was subjected to a saccharification reaction in a saccharification unit, and unreacted lignin was separated therefrom, thereby producing glucose. The PTL, a pentose, was subjected to a monomerization process, and then concentrated under a vacuum of 50 torr. Next, the PTL was subjected to an adsorption process using activated carbon in order to further remove acetic acid that is a fermentation inhibitor, thereby producing xylose.

In the vacuum concentration process, furfural that is a fermentation inhibitor was removed by 90% or more, and acetic acid was removed by 35%. In the subsequent adsorption process, acetic acid could be removed by up to 70%, and HMF could be removed by up to 88%.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for producing cellulosic sugar from biomass by impurity removal and sugar separation, the method comprising the steps of:
   (a) pretreating the biomass hydrothermally, and then separating pretreated liquid (PTL) containing a xylo-oligomer (enzymatic saccharification inhibitor) as a main component and a pretreated biomass (PTB) containing cellulose and lignin as main components;
   (b) monosacchrifying the PTL at a temperature of 90-140° C., vacuum concentrating the monomerized PTL at a pressure of 100-300 torr to remove first impurities, and then removing second impurities from the PTL by adsorption, thereby obtaining xylose; and
   (c) secondly pretreating the PTB, saccharifying the pretreated PTB by a cellulose saccharification—an enzyme, and then separating lignin from a hydrolysate, thereby obtaining glucose; and
   d) introducing partially monomerized PTL into the saccharification process of step (c), after the monosaccharification process of step (b).

2. The method of claim 1, further comprising a step of introducing a non-saccharified substance comprising xylo-oligomer resulting from the adsorption of step (b), into the saccharification process of step (c).

3. The method of claim 1, wherein the concentration of step (b) is a vacuum concentration process, and the first impurities are one or more selected from the group consisting of acetic acid, hydroxymethyl furfural (HMF), and furfural.

4. The method of claim 1, wherein the adsorption of step (b) is performed using activated carbon as an adsorbent, and the second impurities is either acetic acid or hydroxymethyl furfural (HMF).

5. The method of claim 1, wherein a concentration of xylose in step (b) is 5-50 wt %.

6. The method of claim 1, wherein the concentration of glucose in step (c) is 5-12 wt %.

* * * * *

UNITED STATES PATENT AND TRADEMARK OFFICE
CERTIFICATE OF CORRECTION

| | | |
|---|---|---|
| PATENT NO. | : 10,150,978 B2 | Page 1 of 1 |
| APPLICATION NO. | : 15/342356 | |
| DATED | : December 11, 2018 | |
| INVENTOR(S) | : Min Su Koo | |

It is certified that error appears in the above-identified patent and that said Letters Patent is hereby corrected as shown below:

In the Claims

Column 6, Line 45, Claim 1, after "xylose;" delete "and"

Column 6, Line 47, Claim 1, delete "saccharification-an" and insert -- saccharification --

Signed and Sealed this
Sixteenth Day of April, 2019

Andrei Iancu
*Director of the United States Patent and Trademark Office*